United States Patent
Fontenot et al.

(10) Patent No.: US 6,597,941 B2
(45) Date of Patent: *Jul. 22, 2003

(54) TRANSILLUMINATION OF BODY MEMBERS FOR PROTECTION DURING BODY INVASIVE PROCEDURES

(75) Inventors: Mark G. Fontenot, Lafayette, LA (US); Richard Feinberg, Bellingham, WA (US)

(73) Assignee: Stryker Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/391,882

(22) Filed: Sep. 7, 1999

(65) Prior Publication Data

US 2002/0099293 A1 Jul. 25, 2002

Related U.S. Application Data

(63) Continuation of application No. 08/951,759, filed on Oct. 16, 1997, now abandoned, which is a continuation of application No. 08/305,164, filed on Dec. 8, 1994, now abandoned, which is a continuation-in-part of application No. 08/305,296, filed on Sep. 15, 1994, now Pat. No. 5,517,997.

(51) Int. Cl.[7] .................................................. A61B 5/00
(52) U.S. Cl. ........................ 600/473; 600/476; 128/899
(58) Field of Search ................................ 600/473, 476, 600/478; 128/899

(56) References Cited

U.S. PATENT DOCUMENTS 4,541,438 A * 9/1985 Parker et al. ............... 600/473
5,517,997 A * 5/1996 Fontenot ..................... 600/473

* cited by examiner

Primary Examiner—Ruth S. Smith
(74) Attorney, Agent, or Firm—Flynn, Thiel, Boutell & Tanis, P.C.

(57) ABSTRACT

An apparatus and method for identifying a body member during a body intrusive procedure includes infrared light energy which is applied to the body member. Substantially visible infrared free light is introduced into the region. The body member is located by detecting the infrared light energy applied thereto. The infrared light energy may be applied to the body member via a light guide which is inserted into or placed in contact with the body member. In addition, a body member to be located may be illuminated from one side and the location of the illuminator detected by a probe on the other side of the body member.

16 Claims, 8 Drawing Sheets

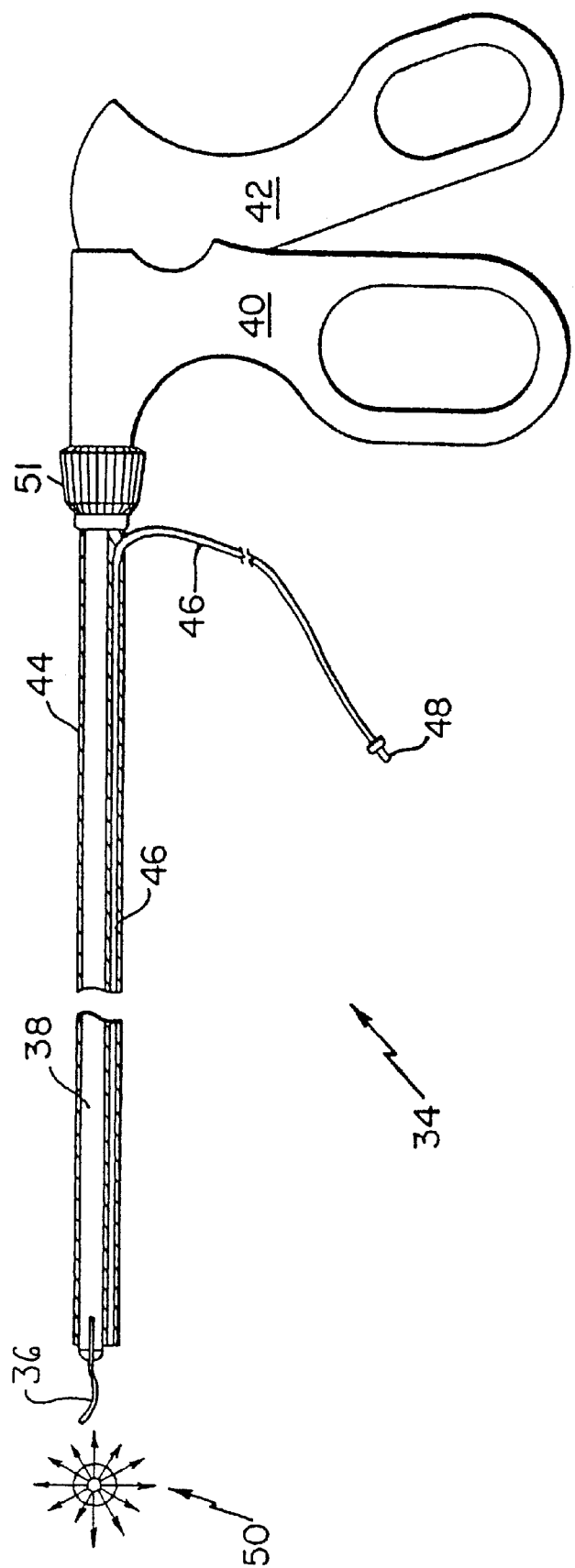

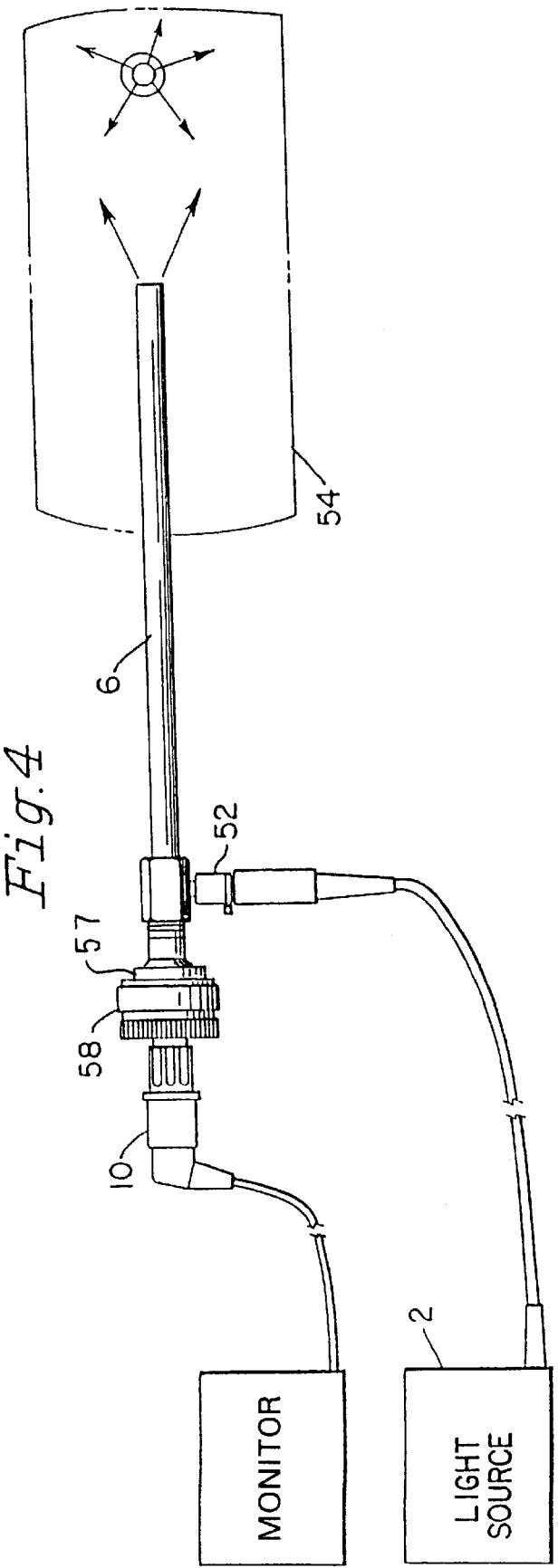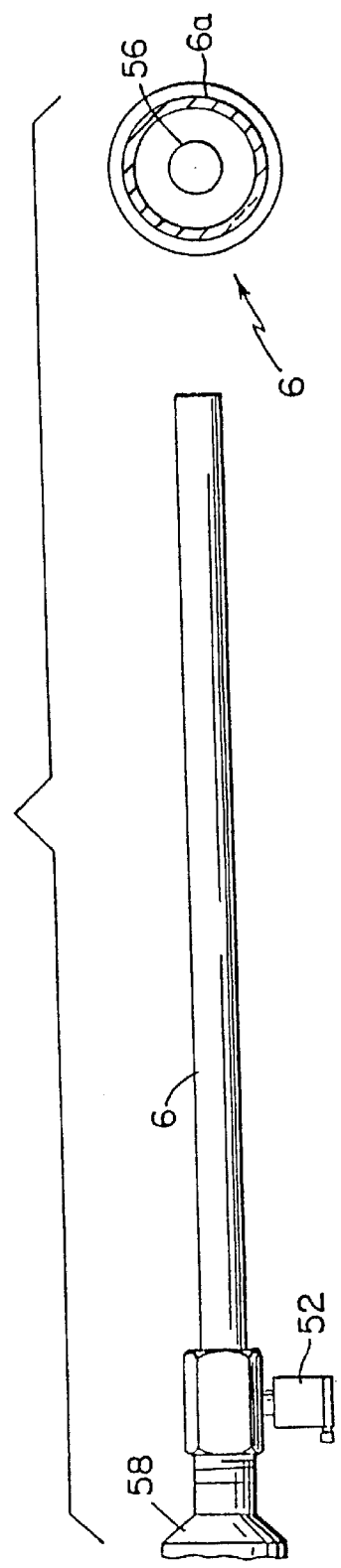

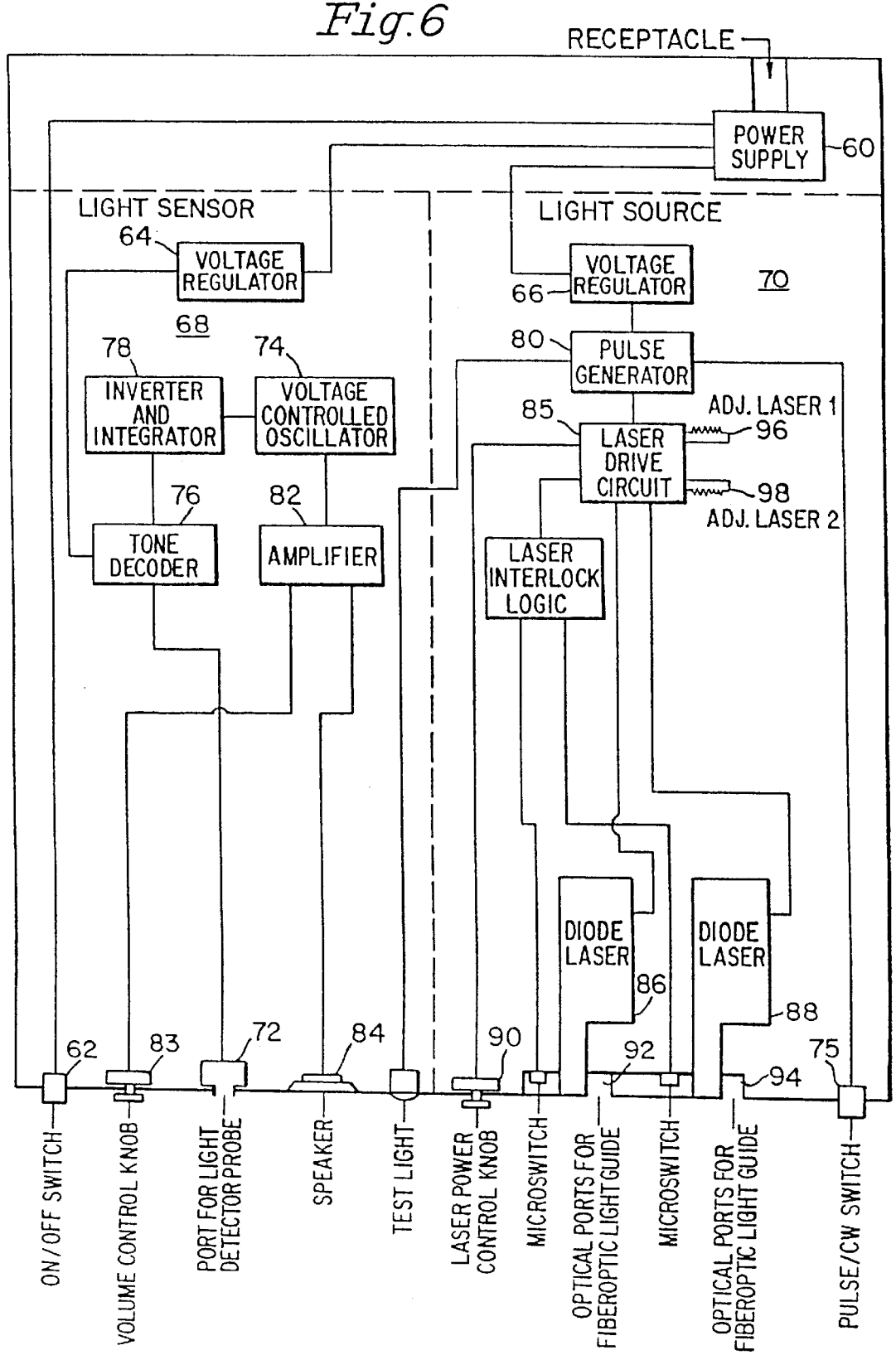

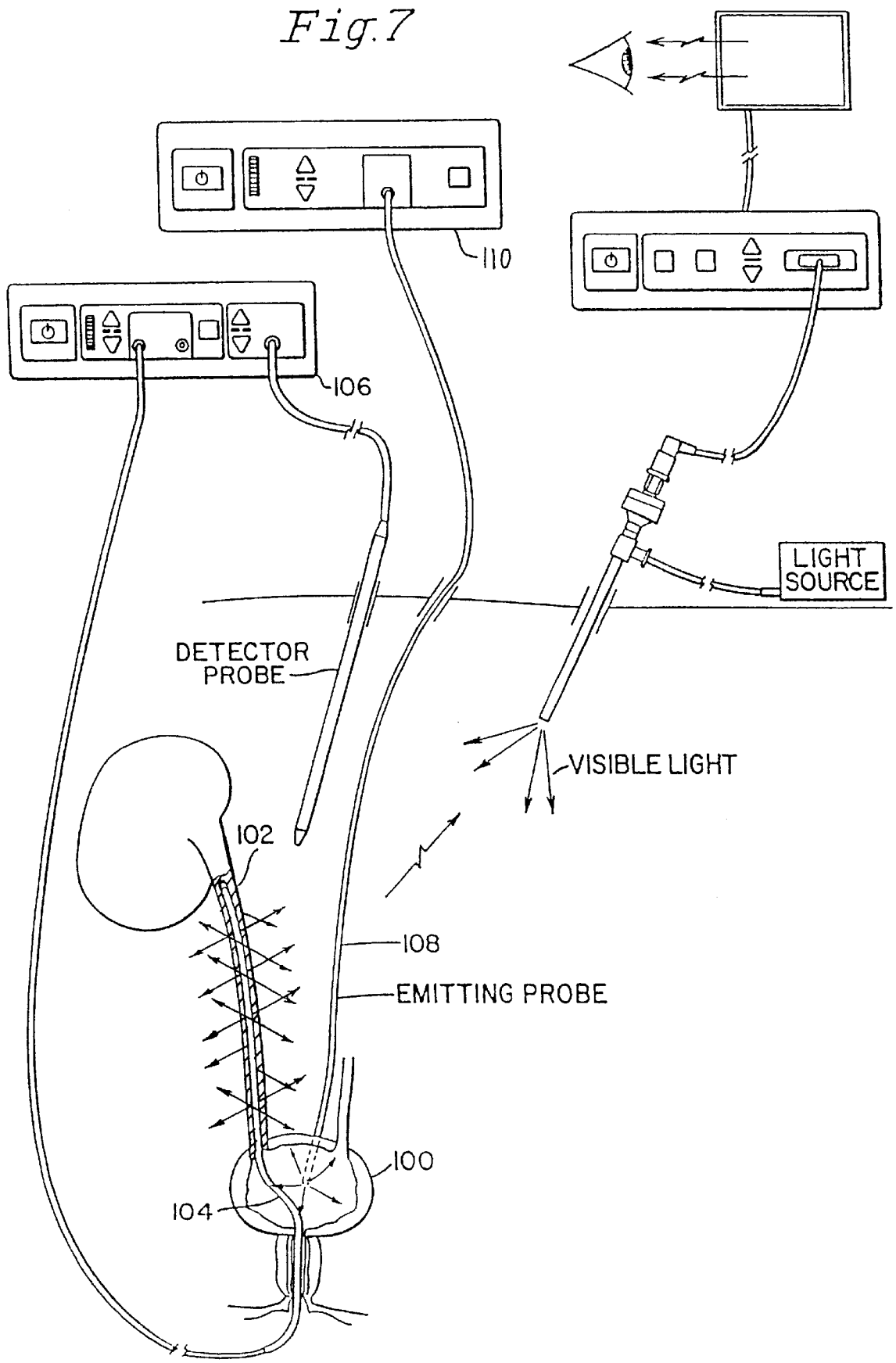

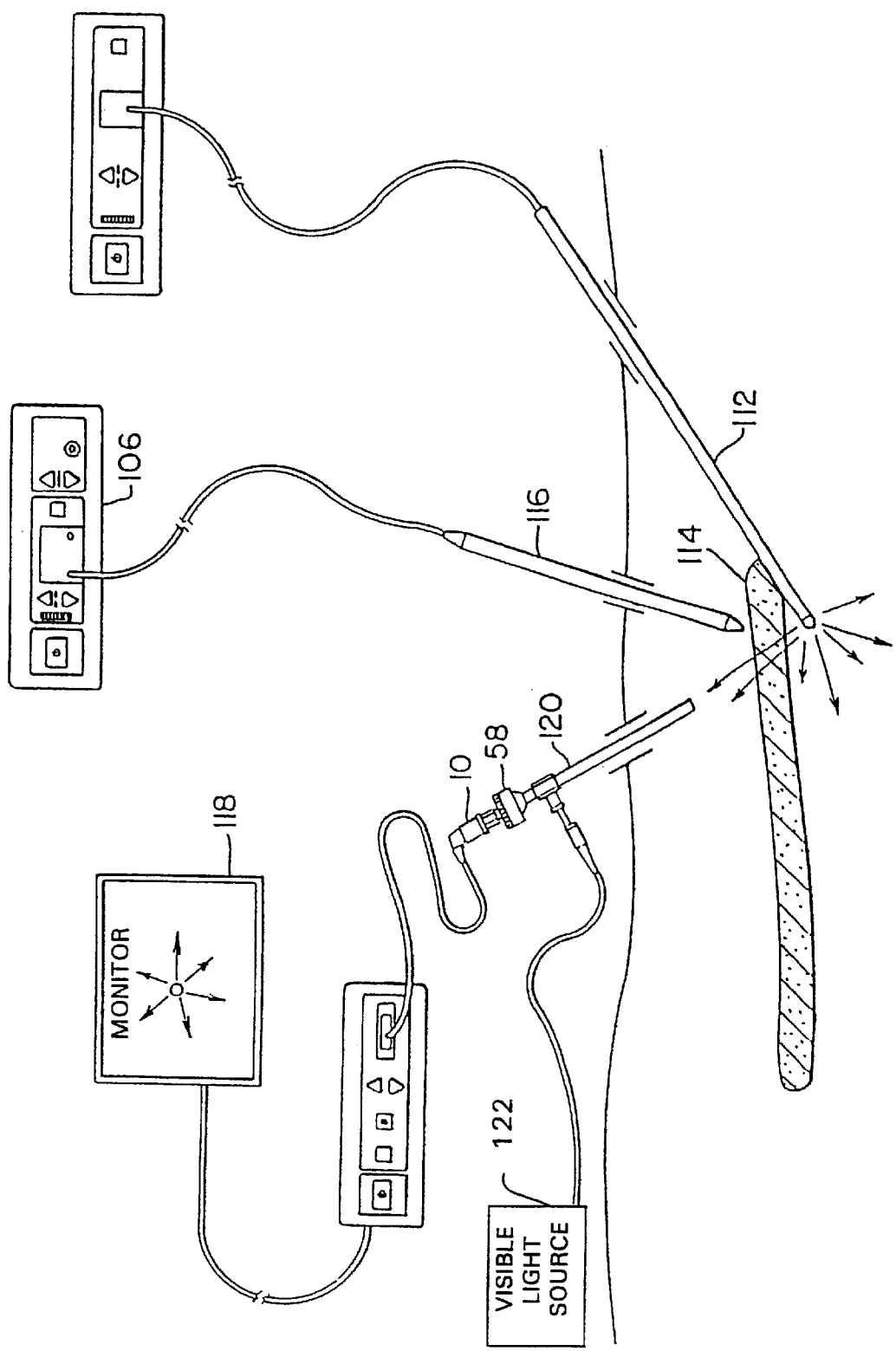

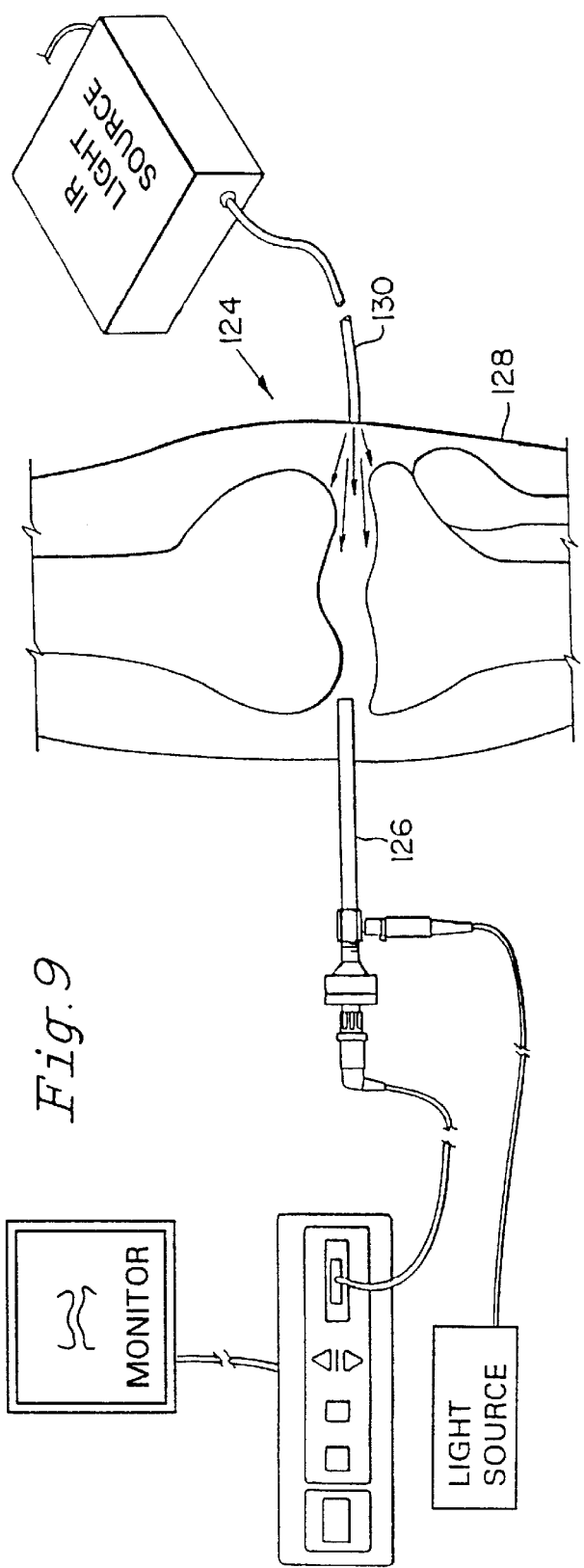
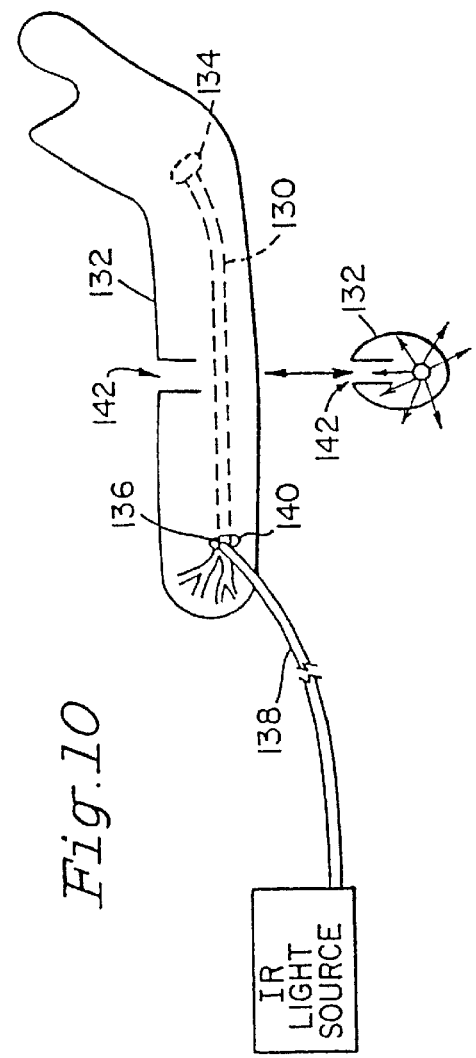
Fig.9
Fig.10

TRANSILLUMINATION OF BODY MEMBERS FOR PROTECTION DURING BODY INVASIVE PROCEDURES

RELATED APPLICATIONS

This application is a continuation of U.S. application Ser. No. 08/951,759, filed Oct. 16, 1997, now abandoned, which is a continuation of U.S. application Ser. No. 08/305,164, filed Dec. 8, 1994, now abandoned, which is a continuation-in-part of U.S. application Ser. No. 08/305,296, filed Sep. 15, 1994, now U.S. Pat. No. 5,517,997, and is related to U.S. application Ser. No. 08/190,516, filed Feb. 2, 1994, now U.S. Pat. No. 5,423,321.

FIELD OF THE INVENTION

The present invention relates to a method and apparatus for transillumination of various parts of a living body to avoid damaging such parts during an invasive procedure and more specifically to the use of two different light sources in such procedures.

BACKGROUND OF THE INVENTION

Although the present invention is described in connection with protection of a ureter during a surgical procedure, this is done merely for purposes of ease of illustration; the invention being useful for protection of various body parts lying adjacent to a region subjected to an invasive procedure.

Currently practiced methods and devices used to transilluminate the ureters to permit ready location and thus protection of the ureter during endoscopic procedures require the cystoscopic placement of a catheter housing and a fiber optic light guide into the lumen of the ureter. The distal portion of the fiber optic light guide is treated to allow light preferably to emit circumferentially from the wall of the fiber. The proximal end of the fiber is coupled to a visible light source. A second light source is coupled to an endoscope and introduced into the surgical site.

Light detection of the transilluminated ureter using typical illuminating catheters such as the Bush DL™ Ureteral Illuminating Catheter Set coupled to a light source during endoscopic procedure is facilitated with a camera. The camera projects the detected image of the transilluminated ureter on a monitor for visualization. Sufficient light from the predicate devices must traverse the ureter and overlying tissues with ample intensity to penetrate surrounding tissue and to overcome the illuminated field from the endoscopic light for the camera to detect light emanating from the transilluminated ureter. In the presence of the normally illuminated operative field from the endoscopic light, the camera frequently cannot detect light emanating from the transilluminated ureter. In an attempt to optimize and intraoperatively improve the performance of their device, Cook Urological, Inc., suggests that it may be necessary to dim or eliminate the endoscopic light illuminating the surgical field. The same problems are encountered in open field surgery where the overhead lights in the operating room may have as great an effect as the endoscopic light source.

OBJECTS OF THE INVENTION

It is an object of the present invention to permit ready detection of preferably both an infrared light source as well as a more standard light source as opposed to only an endoscopic light source during an invasive procedure in a region of a body adjacent the ureter or other body member to be protected.

It is another object of the present invention to provide a system and method permitting ease of discrimination of light energy emanating from a body member to be protected during an invasive procedure adjacent said body member from light introduced to illuminate the region of the procedure adjacent such body member.

It is yet another object of the present invention to protect a body member during a surgical procedure adjacent thereto by emitting modulated electromagnetic radiation from such member to permit ready detection of such radiation in the presence of visible light illuminating the area of the procedure.

Still another object of the present invention is to transmit infrared light through a body part to be protected during a surgical procedure and to maintain the surgical site otherwise free of infrared energy by filtering out infrared energy from an endoscopic or other light source if such is employed.

Yet another object of the present invention is to transmit continuously electromagnetic energy through a body member to be protected during an invasive procedure in a region adjacent thereto and to pulse a light employed to illuminate the region during the procedure.

Another object of the present invention is to synchronize emissions of electromagnetic energy from a body to be protected during a surgical procedure in a region adjacent thereto with emission of light into the region for illumination thereof.

Still another object of the present invention is to synchronize a camera shutter with periodic emission of light into a region being subjected to an invasive procedure with periodic emission of detectable energy from a body member to be protected from injury during such invasive procedure.

Yet another object of the present invention is to couple an optical fiber employed to detect light emitted by a source located in a body part to be protected, to a surgical instrument to be inserted into a body cavity in which a procedure is to be conducted.

It is still another object of the present invention to transmit infrared energy through a body member to be protected during surgery into a region illuminated by an endoscopic light source from which infrared energy has essentially been removed.

Another object of the present invention is to employ an infrared energy source to illuminate a region of a body and view the region with a camera sensitive to both visible and infrared light energy.

Yet another object of the present invention is to transilluminate a body member or region with infrared energy to enhance the view of the region whereby to facilitate a surgical procedure.

Still another object of the present invention is to transmit infrared light energy down a nerve to be protected during a surgical procedure to cause the nerve to become an infrared light energy transmitter.

BRIEF DESCRIPTION OF THE PRESENT INVENTION

The use of infrared emission detection is central to the technology of the present invention.

In particular, the technology takes advantage of the inherent transmissivity of infrared through biological tissues in the range from 700 nm to 1,300 nm. Optically, all biological tissues are considered composite structures consisting of a scattering medium imbibed with various molecular components that absorb light at specific wavelengths. The amount of light absorbed by different molecules is dependent on the chemical and physical properties of the molecule. In the visible part of the spectrum (400 to 650 nm), intense absorption due to hemoglobin and light loss caused by scattering prevents transmission of visible light over more than a few millimeters of tissue. In the infrared spectrum above 1,300 nm, water present in tissue acts as an effective absorber of infrared at this wavelength, again limiting the transmission of infrared longer than 1,300 nm to a short distance. In the infrared range of 700 to 1,300 nm, however, a significant amount of infrared light can be transmitted through several centimeters of biological tissue. This window of high transmissivity is due to the lack of lack of molecular components that absorb infrared between 700 nm and 1,300 nm.

The present invention makes use of the fact that infrared energy can be transmitted through several centimeters of biological tissues to implement various procedures such as protection of organs, etc., during invasive procedures adjacent an organ, to transilluminate an organ to locate it and view it and to render nerves visible over a length thereof.

In a first embodiment of the invention a probe is employed to detect infrared energy during a laparoscopic operation. An endoscopic light source is pulsed while continuous emissions of infrared energy are provided from within a body member to be protected, such as a ureter, duct, colon, blood vessel or other body member. The visible and infrared light energies are directed by the probe to a video camera and then to a monitor. The endoscopic light source is pulsed on at every other frame or half frame of an interlaced display on the monitor so that every other full frame or half frame displays both the member to be protected and the area of the operation and the next frame or half of the interlaced frame displays only the emission from within the body member to be protected. Thus, the body member emission is enhanced.

In a second embodiment of the invention an infrared light energy source is disposed in a body member to be protected during surgery or other invasive procedure in the region of said body member and is pulsed on when visible light from the endoscopic light source is projected into such region is off and vice versa. The on-time of the source in the body member is synchronized with operation of the shutter of a video camera employed to protect an image of a body member on a monitor. In this arrangement, the body member and the region of the invasion of the body are displayed in alternate frames on the monitor. As will become apparent below, elimination of infrared energy from the endoscopic light source further enhances visualization of the member to be protected.

In the event the procedure involved is an open body procedure and the visible light source is the standard overhead array of lights in an operating room, the visible lights cannot be pulsed and therefore only the infrared source is pulsed. The detectors then must be sensitive only to infrared and/or to a 12 KHz signal imposed on the infrared light.

In another embodiment of the invention, the light fiber employed to detect light transmitted through a body member in the surgical area is secured to a surgical instrument to be inserted into and used in such area. The fiber may be carried by a sleeve slipped over the instrument which may be a scissor, a stapler, or the like. The fiber may be mounted so as to be forward looking. Alternatively, single or multiple fibers may be mounted so as to be side looking or forward and side looking as determined by the requirements of the surgical site and instrument.

In still another embodiment of the invention, an audible alarm is used in the former two embodiments of the invention and is synchronized with the infrared light source. Thus, such alarm does not respond to infrared energy of the endoscopic light source and the level of infrared energy to produce detection may as a result be reduced to provide information at an even greater distance from the member to be protected than might otherwise be the case. The alarm may be of constant amplitude or may vary as a function of the distance of the probe from the infrared emitter.

In a further preferred embodiment of the invention, infrared light energy is transmitted through a body part to be protected during laparoscopic procedures while the rest of the surgical site is infrared free, this being accomplished by removing infrared energy from the light emitted by the endoscopic light source employed to illuminate the surgical site. This effect is achieved by employing an infrared blocking filter between the endoscopic light source and the surgical site. In this embodiment, and useful in the other embodiments, the endoscope has an annulus of optic fibers for conducting light from an endoscopic light source to the surgical site and a centrally located lens for transmitting light from the surgical site to a CCD of a video camera, the lens having a focal length to accommodate the length of the endoscope.

In such embodiment of the invention the infrared blocking filter may be inserted into the light path from the endoscopic light source whereby infrared light energy from an emitter in or adjacent to an organ or the like to be protected will be the only substantial source of infrared energy in the operative region. Thus, response of the alarm will be limited to infrared energy from the body to be protected. Further, the video camera is made sensitive to both visual and infrared energy so the infrared energy source will be clearly identified.

The present invention also discloses the use of transillumination of a region subject to a surgical procedure. In one such illustrative application an infrared energy source is inserted into the region of the knee joint and an infrared energy probe connected to a video camera and monitor is either inserted into the opposite side of the joint or placed on the surface of the skin on the oppose side of the joint. Because the articular cartilage and surrounding tissues are generally white and translucent with not great color contrast, the transillumination yields improved overall illumination of the surgical site while improving definition of the structures lying between the source and the probe.

In a laparoscopic procedure, the location of an infrared energy source used to transilluminate internal organs, tissues, bones, etc., may be detected by an infrared detector probe and positioning is rendered less difficult. An endoscopic source and detector probe may then be accurately positioned in the operative region for detection of the region to be treated.

In the protection of nerves, it has been found that when an infrared energy emitter is placed in contact with a nerve, the infrared energy is transmitted along the nerve, which then becomes an infrared energy emitter along a length thereof, thus identifying the location of such length. The length of the nerve that is thus identified depends upon the energy of the infrared energy source.

The infrared energy source in the original system of the present invention was a 5 milliwatt source. The system has been configured to utilize a 1 watt source and in fact uses two such sources. In tests conducted to date only 256 mW have been used. The second source is used to transilluminate an organ such as the bladder while an infrared emitter is inserted for instance in the ureter. The transillumination may assist in locating various members at the actual surgical site. Thus, blood vessels, ligaments, ducts, stones in various organs, all or any one of which may be involved in the surgical procedure can be located while at the same time the ureter, etc., are protected utilizing the other laser source.

In all of the above embodiments a polarizing filter may be placed in the light path to the camera to reduce glare.

All of the above systems may be operated with NTSC, PAL or SECAM video systems so that, as appropriate, frames may be interlaced as indicated hereinafter, if so desired.

The above and other features, objects and advantages of the present invention, together with the best means contemplated by the inventor thereof for carrying out the invention, will become more apparent from reading the following description of a preferred embodiment and perusing the associated drawings in which:

BRIEF DESCRIPTION OF THE DRAWINGS

FIG. 3 illustrates a surgical scissor with a fiber bearing sleeve disposed about the instrument;

FIG. 4 illustrates the endoscope and related equipment provided in accordance with the present invention;

FIG. 5 illustrates a side and end view of the endoscope employed with adapters that can accommodate various filters;

FIG. 6 illustrates a block diagram of the control circuits of a preferred embodiment of the invention;

FIG. 7 illustrates the preferred embodiment utilizing the light from both diode lasers of FIG. 6;

FIG. 8 illustrates the use of the IR emitter and probe to locate a body to be subject to a procedure;

FIG. 9 illustrates the use of the present invention to illuminate and view a knee joint during arthroscopic surgery; and FIG. 10 illustrates the use of IR energy to define the location of a nerve or nerve bundle.

DETAILED DESCRIPTION OF THE PRESENT INVENTION

Figure 1:
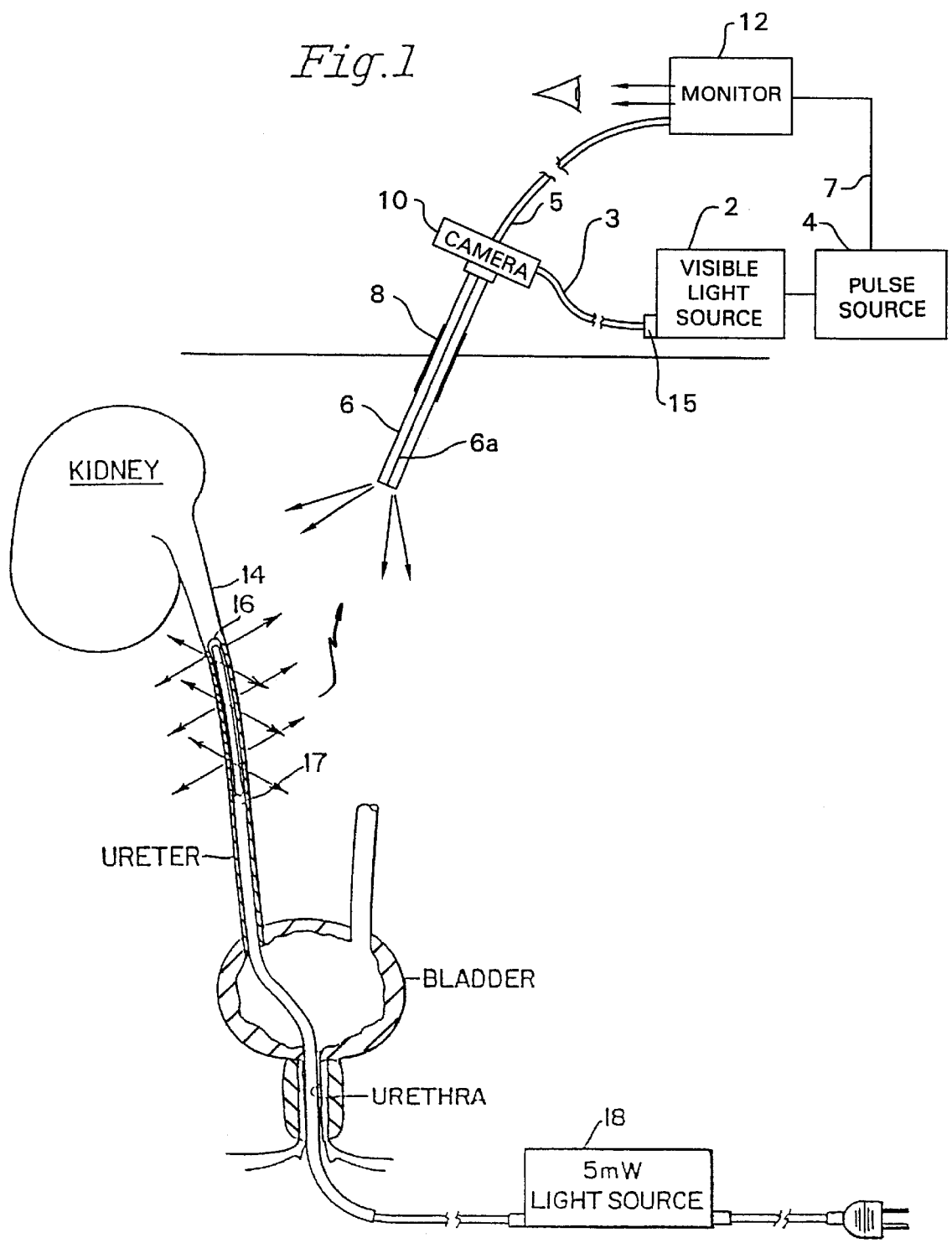
FIG. 1 illustrates a first embodiment of the present invention.

Referring specifically to FIG. 1 of the accompanying drawings, there is illustrated a diagram of a system employing a pulsed laparoscopic visible light source 2. The source 2 is turned on and off by a source of energizing pulses 4 at a rate that is synchronized with the frame rate of a monitor 12 via lead 7.

The endoscope 6 consists of a lens system surrounded by a fiber optic bundle 6a. The light cable 3 couples the endoscopic light source 2 to the fiber optic bundle 6a of the endoscope. During endoscopic procedures, the surgical field is illuminated using the endoscope 6 coupled to the endoscopic light source 2 via the light cable 3. Specifically, the distal end of the endoscope 6 is located internally of a body in a region to be illuminated. The proximal end of the endoscope 6 has an adapter 51 (FIG. 3) that couples the distal end of the light cable 3 to the proximal end of the internal fiber optic bundle 6a of the endoscope 6. The proximal end of the light cable 3 is coupled to the light source 2. Light exits the most distal end of the fiber optic bundle 6a at the distal end of the endoscope 6. The lens system of the endoscope 6 transmits the illuminated surgical field to the monitor via the camera 10 and the cable 5.

Standard endoscopic optics direct light supplied by the light source 2 and reflected by the body tissue in such regions to the camera where the signals are processed and displayed on the monitor. Normally such cameras have a filter over the sensing chip to block out infrared. In this instance, such filter is not used so that the camera can respond to energy of such wavelengths emitted from the fiber optic light guide 6a as well as to visible light. In such a case an IR filter normally found in video cameras is removed from the CCD of the camera and is replaced by a sapphire window placed over the CCD to render it responsive to both IR and visible light. In order to insure that that the only source of IR in the surgical field is emitted by the light guide 17, an infrared energy filter 15 is inserted into the light path from the source 2.

In the illustrated example of a laparoscopic procedure in FIG. 1, the body member to be protected is a ureter designated by reference number 14. A catheter 16 is inserted into the ureter and a fiber optic light guide 17 is inserted into the catheter and may be conditioned to emit infrared energy in all directions as fully disclosed in said parents of this application, the full disclosure of which is incorporated by reference. The infrared energy is supplied by a 50 mW to 250 mW infrared light source 18 coupled to the fiber optic light guide 17.

In operation of the system, the continuous infrared energy is transmitted to the fiber optic light guide 17 and via light guide 6 (see discussion of FIG. 2) to the video camera which provides an image of the screen of the monitor 12. The intermittent visible light is also displayed on the monitor thereby displaying a view of the region being investigated but the display of the infrared image is stronger and readily locates the ureter in this case in the field of view appearing on the monitor. During the period the light source 2 is turned off, the display of the infrared light emitted through the ureter clearly predominates. When IR is removed from the light supplied by source 2, pulsing of this source is no longer necessary and the IR source may be pulsed to render it more readily detected. This latter embodiment is preferred.

Figure 2:
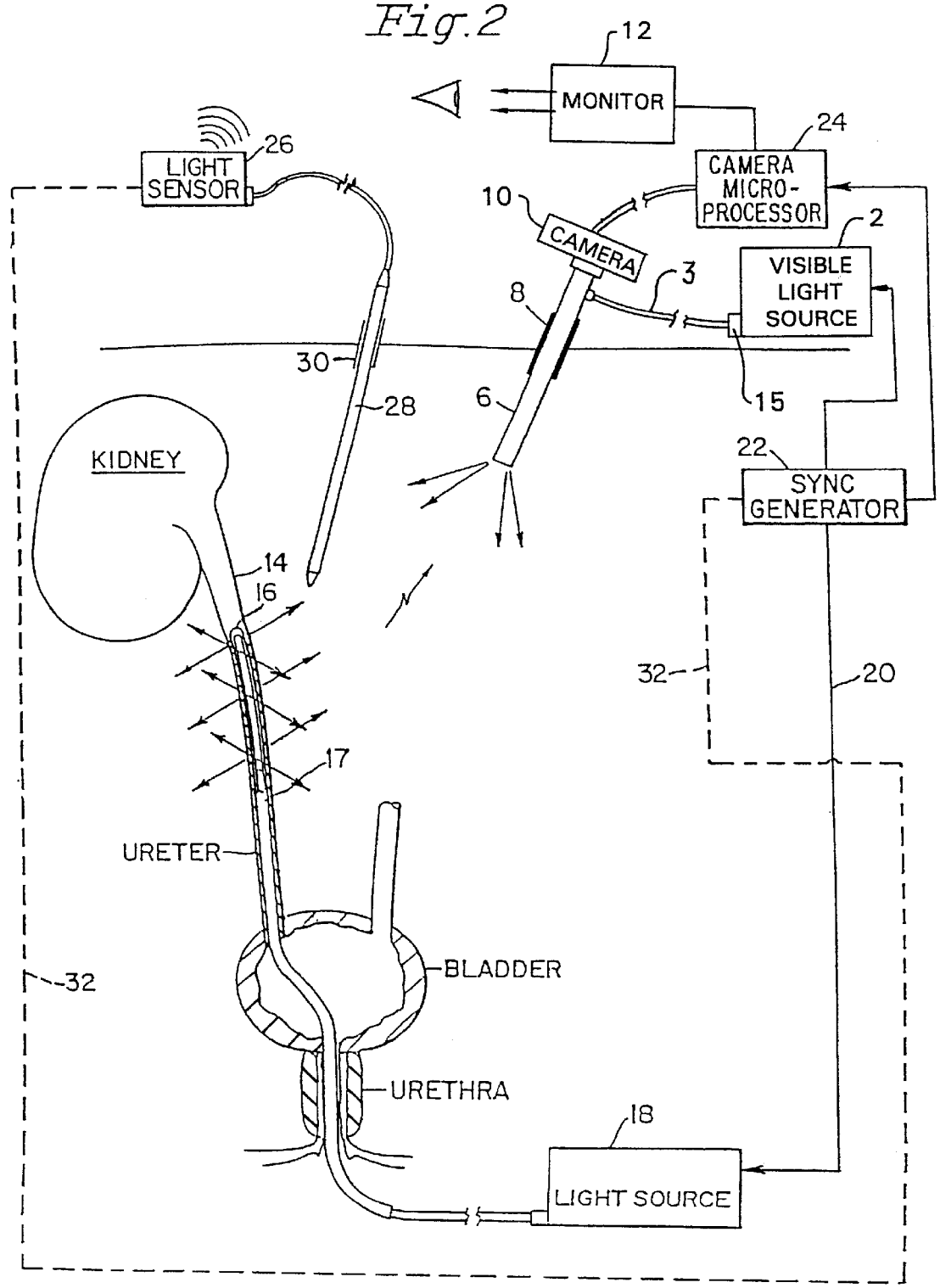
FIG. 2 illustrates a second and a third embodiment of the present invention.

Referring to FIG. 2 there is illustrated a second embodiment of the present invention employing synchronization of various elements of the system. Again, light source 18 supplies infrared energy to the fiber optic light guide 17 but the source 18 is pulsed via a lead 20 from a sync generator 22. The sync generator 22 provides pulses to a camera microprocessor 24 that controls the shutter of the camera 10 and the sweep of the monitor 12. The sync generator 22 also controls the energization of the light source 2. Further, there is provided an infrared light sensor 26 that produces an audible sound (and/or visual display) whenever infrared is transmitted thereto via a light guide 28, also introduced into the region of interest via a trocar 30.

Note in FIG. 2 a dashed line 32. This line extends from the sync generator 22 and pulses the light sensor 26 in synchronism with the light source 18. With such procedure, the sensor 26 cannot be triggered by light from the endoscope light source 2 and a low threshold may be used so that infrared emission from the ureter may be detected at a greater distance than would be possible otherwise.

In operation, the sync generator 22 alternates energization of the light sources 2 and 18 so the infrared light source 18 is on when the endoscope light source is off and vice versa.

Such operation provides great flexibility of the display on the monitor. If the camera is turned on only when the source 18 is energized, then only the ureter is displayed. If the camera 10 is turned on only when the endoscopic light source 2 is energized, then only the surgical area is displayed (not a good practice if a body member is endangered by the procedure). Alternatively and preferably in this embodiment, the system is configured so the camera 10 is turned on during the activation of each light source so that with proper synchronization, and preferably the use of an NTSC system, the two areas are displayed in alternate interlaced frames on the monitor.

The sync generator 22 may reverse the on/off cycles relative to the opening and closing of the camera shutter. Specifically, maximum view of the ureter is achievable with a reversal of the cycles of the IR source and the endoscope source relative to the camera shutter opening and closing.

TABLE 1

| Camera Shutter | OPEN | CLOSED | OPEN | CLOSED |
|---|---|---|---|---|
| IR Source | ON | OFF | OFF | ON |
| Endoscopic Source | OFF | ON | ON | OFF |

With this arrangement a high degree of differentiation is obtained and reference is made to Table 2 below.

Continuing with a description of the system elements, the probe 28 and associated circuitry from the light sensor provide an audible signal (light may instead be employed), the intensity of which may or may not vary with proximity of the probe 28 to the ureter (see the discussion of FIG. 6). If the signal does vary, the location of the ureter may be determined with greater precision than may be possible with the probe 6—monitor 12 system. The probe 28 shows on the monitor and the relative position of the surgical instrument relative to the ureter is more readily determinable by the position of the surgical instrument relative to the probe 28.

Referring to FIG. 3 of the accompanying drawings, there is illustrated a surgical scissor generally designated by the reference numeral 34. The two blades of the scissor, only one blade 36 being illustrated, are carried at the end of a hollow shaft 38 having the operating mechanism for the scissor disposed therein the scissor is actuated by squeezing together two hand grip members 40 and 42.

A sleeve 44 is slipped over the shaft 38 and carries an optical fiber 46 in a passage formed in the sleeve. An end 48 of the fiber is connected to a light sensor such as camera 10 or light sensor 26 of FIG. 2 or other suitable sensor such as illustrated in U.S. Pat. No. 5,423,321.

The element designated 50 in FIG. 3 is the infrared emitting fiber 17 in the organ to be protected, for instance, a ureter. The fiber 46 illustrated in FIG. 3 is a forward looking fiber but could also be a side looking fiber.

Truth Table, Table 2 below, represents operation of the FIG. 2 System, with the camera shutter open and utilizing a 5 mw light source 18. When both lights are on continuously, the response relative to both of the light sources by the monitor and the audible source is acceptable, but enhancement is preferred. The monitor display does not provide the sharp differentiation that would be preferred.

When only the catheter source is "on", the display of the ureter, in this instance, is clear and sharp since infrared from the endoscopic source does not interfere with the signal generator 26.

If the threshold on the audible detector is low enough, an audible signal may be detected even though the infrared source is off. This problem may be addressed by pulsing the audible signal sources "on" via lead 32 only when the infrared source is energized or by eliminating the IR energy from the light emitted by the endoscopic source. Under either of these circumstances there is no problem with the visual light and the threshold can be set relatively low on this detector.

When the camera shutter is closed the Truth Table 3 on Page 21 applies. Specifically, only the audible signal generator 26 is operative and the response is the same as in the table above.

TABLE 2

Truth Table outlining the performance of the synchronized dual light sources used to transilluminate the ureters during endoscopic surgery. The camera shutter is open.

| Catheter Light Source | ON | ON | OFF |
|---|---|---|---|
| Endoscope Light Source | ON | OFF | ON |
| Visual Detection on Monitor | Marginal Not Efficient | YES | NO |
| Audible Detection Using Light Probe | Marginal Not Efficient | YES | NO but possible |
| Audible Detection Using Pulsed Light Probe | Marginal Not Efficient | YES | NO |
| Endoscope with IR Filter | ON | OFF | ON |
| Visual Detection on Monitor | YES | YES | NO |
| Audible Detection Using Light Probe | YES | YES | NO |
| Audible Detection Using Pulsed Light Probe | YES | YES | NO |

TABLE 3

Truth Table outlining the performance of the synchronized dual light sources used to transilluminate the ureters during endoscopic surgery. The camera shutter is closed.

| Catheter Light Source | ON | ON | OFF |
|---|---|---|---|
| Endoscope Light Source | ON | OFF | ON |
| Visual Detection on Monitor | Marginal Not Efficient | YES | NO but possible |
| Audible Detection Using Light Probe | Marginal Not Efficient | YES | NO but possible |
| Audible Detection using Pulsed Light Probe | Marginal Not Efficient | YES | NO |

The same changes as reflected in Table 2 occur if the IR light energy is filtered from the light emitted by the endoscopic light source. The pulsing of the infrared or a visible light source 18 coupled to the fiber optic light guide 17 greatly enhances the ability of the surgeon or other health care operative to distinguish between light emanating from the infrared source and visual light reflected from the tissue illuminated by light from an endoscopic or ambient light source.

In furtherance of this concept, the audible signal may be modulated with an identifiable signal to insure that the sound does not simply fade into the background of consciousness. For instance, a 1500 cycle per second tone can be imposed on the output during each "on" cycle. This approach reduces the effect of noise from the light sources. The 1500 Hz signal may be applied to a 50% duty cycle 12 KHz square wave.

The audible signal generator could also be a visual light source that would blink at a rate that varies with proximity of the probe to the body member to be protected or just blink when the ureter is approached.

Typical specifications for this system are:

1. A 5 mW infrared LED or two variable 250 mW infrared laser diodes.
2. An infrared emitting segment of 20 to 25 cm.
3. An ST type optical connector on the proximate end of the light detector probe. Both the light probe and guide are manufactured by Ethox Corporation according to the specification.
4. Government regulations for a Class I laser required that the power emitted from the fiber optic light guide should not exceed 60.8 μW from the hottest point on the fiber at a distance of 20 cm through a 7 mm operation.
5. Ureteral catheter—65 cm long with an O.D. of 2.3 mm and three holes for drainage from TFX Medical.
6. The light guide is an Eska Fiber from Mitsubishi.
7. Light source spectrum of 620 nm to 1,000 nm.
8. The camera is a Model 2070D manufactured by Envision Medical Corporation of Santa Barbara, Calif.

A further embodiment of the present invention is illustrated in FIGS. 4 and 5 of the accompanying drawings. The system illustrated in FIG. 4 is similar to that illustrated in FIG. 1 and where appropriate the references numerals of FIG. 1 are employed.

It is the desire of this embodiment to create an essentially infrared free zone, except for emissions from the ureter, in an effort to unerringly distinguish the light from the ureter from any other source. In order to accomplish this result, an adaptor 52 is employed. The light source 2 is a halogen or Xenon light source, both of which are typically right in infrared energy. To eliminate the infrared energy from the source, a Cyon (#2) filter 15 is inserted into the adapter 52 or into the light cable 3, as illustrated, to block the infrared energy. The filter is available from Hoya, No. 8405.

The filtered light is applied to endoscope 6 which transmits the filtered IR free light to the surgical site 54 via fiber optic bundle 6a of FIGS. 1 and 5. A lens system (diagrammatically 56) is disposed inside of the endoscope 6 and focuses light on the CCD of a camera 10 through a camera coupler 58. The camera coupler may have a polarizing filter 57 to minimize glare from the illuminated surgical field. Alternatively, the adapter 52 may be constructed to receive removably the IR filter 15 so that if the system of the present invention is not to be used the filter may be removed.

The system illustrated in FIGS. 4 and 5 is readily adapted to the structure of FIGS. 1 and 2, the endoscope 6 of FIG. 5 focusing the light at the end of the endoscope and directing it via the coupler 58.

In a system employing a 250 mW IR source, marginal or acceptable but not too good results are to a great extent eliminated and more importantly the distance over which the IR energy can be detected is greatly increased. The system to be described may employ 1 watt laser diodes but in the system tested lasers were set at 250 mW. Such a circuit is illustrated in FIG. 6 of the accompanying drawings.

Referring specifically to FIG. 6, a power supply 60 is controlled by an on/off switch 62. The supply 60 provides power to two voltage regulators 64 and 66 associated with an audio section 68 and an IR source section 70, respectively.

The audio section 68 includes a port 72 for a light detector probe, such as probe 28 of FIG. 2. The port feeds a voltage controlled oscillator 74 via a tone decoder 767 and an inverter and integrator 78. The tone decoder passes a signal at the frequency of modulation provided by a pulse generator 80 in the IR section 70, 12 KHz.

The voltage control oscillator provides a fixed frequency whenever the signal from the inverter and integrator element 78 exceeds a certain threshold. A variable frequency may also be employed, if desired. The signal developed by the integrator 78 is supplied to the VCO and thence to an amplifier 82 feeding a speaker 84 or perhaps a light. The frequency output of the VCO can vary between 440 Hz and 4400 Hz but, as indicated above, is currently set to a single tone. A volume control 83 controls the output signal from the amplifier 82.

Referring now to the IR source section 70, the voltage regulator 66 is coupled to pulse generator 80. The pulse generator can be switched between continuous wave or pulsed operation. In the pulsed mode operation may be at 4 Hz with a 23 KHz tone. In the continuous mode a 12 KHz signal with or without 1500 Hz tone is emitted. The pulse generator imposes the tone on the signal produced by the generator. The pulse generator supplies its output signal to a laser driver circuit 85. The drive circuit drives two laser diodes 86 and 88. Although 1 watt lasers may be employed, the laser diodes currently employed are set to operate at a maximum power of 250 mW. Potentiometers 96 and 98 on the laser drive circuit 85 are employed to initially set the maximum output of the laser diodes. Once the maximum output it set, the wattage output may be varied from 50 mW to 250 mW; control being affected by a laser power control operated by a knob 90. The IR outputs from the laser diodes 86 and 88 are supplied to probes, such as the probe 28 of FIG. 2 via ports 92 and 94, respectively.

Simulated tests have been conducted to determine the relative effectiveness of the prior art ureteral detectors, inventor's prior system and the system of FIG. 6. A piece of bovine muscle was used of a thickness that permitted detection by the prior art Bush devices from Rusch, Inc. and Cook Urological. Tests were conducted using a Stryker 782 Solid State Color Medical Video Camera coupled to a Quantum 3000 light source to transilluminate the specimen. Display was on a Sony 13" monitor and/or an audible signal was used for detection.

The performance of the various devices was as follows:

TABLE 4

| System | Dim Overhead Lighting | Full Overhead Lighting |
| --- | --- | --- |
| Detector Probe Coupled to the IR Illuminator | 30 mm | 30 mm |
| Bush Ureteral Illuminator (Rusch, Inc.) | 8 mm (very faint) | 4 mm |
| Bush DL ™ Illuminating Catheter (Cook) | 8 mm (very faint) | 4 mm |

TABLE 5

Comparison of the system of FIGS. 2 and 5,
Bush Ureteral Illuminator (Rusch, Inc.), and the Bush DL ™
Ureteral Illuminating Catheter (Cook Urological), under
simulated laparoscopic procedures.

| System | Dim Laparoscopic Lighting | Full Laparoscopic Lighting |
|---|---|---|
| Detector Probe Coupled to the IR Illuminator | 30 mm | 30 mm |
| Imaging System | 12 mm | 8 mm |
| Bush Ureteral Illuminator (Rusch, Inc.) | 8 mm (very faint) | 4 mm |
| Bush DL ™ Ureteral Illuminating Catheter (Cook) | 8 mm (very faint) | 4 mm |

Transillumination and electronic detection of the test tissue using the system of FIG. 6 is approximately three-fold more efficient when compared to the Bush Ureteral Illuminator (Rusch, Inc.), and the Bush DL™ Ureteral Illuminating Catheter (Cook Urological), under simulated open and laparoscopic procedures. It should also be noted that detection by the apparatus of FIG. 6 did not vary over the 30 mm range. The apparatus of FIG. 2 was twice as sensitive of the prior art devices.

In the preferred embodiment of the invention the light from the endoscope has the IR light energy removed and the camera is sensitive to both IR light and visible light energy. When performing a laparoscopic procedure, pulsing is not essential but is preferred and also a polarizing filter may be used to reduce glare.

In an open body procedure, infrared light energy can, but not readily, be filtered from the light emitted by the overhead lights and pulsing of at least the infrared light energy source is strongly preferred. The polarizing filter 57 may also be used.

The signals from the CCD may be processed in a variety of ways to enhance the visibility of the infrared image. Such enhancement may include contrast enhancement, additional gain, digital edge detection, addition of pseudo-color, use of the full 1 watt of the laser diode and the like.

Referring now specifically to FIG. 7 of the accompanying drawings, there is illustrated the use of the second diode laser of FIG. 6. In the situation illustrated, surgery is to be performed on a bladder designated by reference number 100. Ureter 102 is illuminated by light fiber 104 from a light source 106. The bladder 100 is transilluminated by a second light probe 108 energized by a second laser from a source 110. In practice, the two sources are those illustrated in FIG. 6 and would usually be enclosed within a single case.

Except for the second source, the system will be that illustrated in FIGS. 2 and 5 combined. The second IR source permits the surgeon to clearly see the site of the operation and the interior of the organ to be treated. In such a situation the full 1 watt of energy of the laser supply probe 100 may be employed.

Referring specifically to FIG. 8 there is illustrated another example of use of the present invention to transilluminate tissue to be inspected or operated upon.

An IR emitting light probe 112 is inserted into the body and the probe 112 is to be positioned in a specific location behind tissue 114. An IR detector probe 116 is also inserted into the body on the opposite side of the tissue 114 from the probe 112. The emitting probe 112 is maneuvered into the desired position with the help of detector probe 116. The site of the operation is viewed on monitor 118 by use of endoscope 120 and associated members including visible light source 122. The use of the IR emitting probe 112 and detector probe 116 permits the position of probe 112 to be determined at all times particularly during a scanning procedure.

A particularly useful approach to arthroscopic surgery employing the apparatus of the present invention is illustrated in FIG. 9 of the accompanying drawings. A knee joint 124 to be repaired is viewed by an endoscope 126 inserted into leg 128 in alignment with the joint 124 to be repaired. The joint is flooded with infrared light by a light probe 130 positioned preferably against the skin of the leg 128 opposite the joint 124 and thus on the opposite side of the joint from the endoscope 126.

The emitting probe 130 is finished with a flat end placed against the skin outside the body. Because the articular cartilage and surrounding tissues are generally "white and translucent" with less color contrast when compared to laparoscopy, the back transillumination yields improve overall illumination of the viewed surgical site while providing back transillumination of structures between the emitting probe and the endoscope. Applying the infrared light through the skin diffuses the light and produces good overall illumination of the skin.

Referring to FIG. 10 there is illustrated a procedure for protecting nerves from damage during invasive procedures. It has been found that if an IR light emitting probe is brought into contact with a nerve, IR energy is transmitting along the nerve and it becomes an IR emitter.

In the peripheral nervous system, nerve fibers are grouped in bundles to form the nerves. Nerves have a translucent and whitish appearance because of their myelin content. It is imperative that they are not inadvertently damaged during surgery. As an example, and reference is made to FIG. 10, the inferior alveolar nerve 130 enters the lower jaw or mandible 132 posteriorly through the mandibular foramen 134. It gives sensory nerve supply or innervation to the gums and teeth of the mandible. The inferior alveolar nerve 130 exits the mental foramen of the mandible anteriorly as the mental nerve 136 giving sensory innervation to the skin over the chin and the lower lip.

Over one million dental implants are placed in the mandible per year. Frequently, during dental implant placement procedure, it is important to locate the interior alveolar nerve as it courses in the mandible. Obviously, if an implant is placed in the mandible that transects or compresses the inferior alveolar nerve, then ensuing and irreversible sensor loss (feeling) to the lower lip and chin may follow. Thus, locating the inferior alveolar nerve prior to implant placement has significant clinical advantages.

The apparatus of FIG. 10 illuminates the inferior alveolar nerve 130 using an infrared emitting probe 138 with a spherical end. The infrared emitting probe is placed against the mental nerve 136 as it exits the mental foramen 140. The inferior alveolar nerve 130 is transilluminated posteriorly. During the operative procedure, either the imaging system or the detector probe coupled to the detector panel of the IR illuminator peers into a prepared bony site 142 that receives the implant. If the inferior alveolar nerve is detected, then the surgeon can take precautions against injury, i.e., stop drilling or use a shorter dental implant. Thus, the illumination of a length of the nerve permits it to be viewed and preserved. The procedure is applicable to protection of important nerve structure wherever located.

The device disclosed herein will often be sold as an article of commercial in kit form in which various elements may be sold as a package. Such could include the light source, the fiber for insertion into an organ, vessel or the like, a catheter which may or may not be used with the aforesaid light fiber, a camera, camera microprocessor, sync generator light source, light sensor, pulse generator and/or audible or visual proximity sensor with ancillary equipment as required.

The article may be that illustrated in FIG. 1, or FIG. 2, the sleeve of FIG. 3 or additional equipment of FIGS. 4 to 10.

Once given the above disclosure, many other features, modifications and improvements will become apparent to the skilled artisan. Such features, modifications and improvements are, therefore, considered to be a part of this invention, the scope of which is to be determined by the following claims.

What is claimed is:

1. An apparatus for identifying a body member located adjacent a surgical site comprising:
    a first light energy source configured to emit infrared light energy having a wavelength between 700 nm to 1300 nm;
    a first light guide connected to said first light energy source for receiving the infrared light energy and constructed to apply the infrared light energy to the body member so the infrared light energy penetrates and is emitted through the body member;
    a second light energy source configured to emit light energy having a wavelength different than the wavelength of the infrared light energy emitted by the first light energy source;
    a filter configured to filter infrared light energy from the light energy emitted by said second light energy source so that said filter emits substantially infrared free light energy;
    a light emitter configured to introduce the substantially infrared free light energy into the surgical site;
    a video camera sensitive to both received infrared free light energy and infrared light energy that is configured to generate image-defining video signals based on the received infrared free light energy and on the infrared light energy emitted through the body member;
    a video monitor configured to receive the video signals and display an image defined by the video signals.

2. The apparatus according to claim 1 further including a polarizing filter positioned between said second light guide and said camera.

3. The apparatus according to claim 1 wherein at least one of the first and second light energy sources is configured to emit light energy in a pulsed pattern.

4. The apparatus according to claim 1 wherein said first light guide is configured to be placed in contact with the body member to be identified.

5. The apparatus according to claim 1 wherein said first light guide is configured to be inserted into the body member to be identified.

6. An apparatus for identifying a body member located in a region of an intrusive procedure in a body in which the body member is located comprising:
    a first source of light energy configured to provide infrared light energy in a range of 700 nm to 1300 nm;
    a fiber optic light guide connected to said first source of light energy and configured to be insertable into the body member and to emit the infrared light energy within the body member so that the infrared light energy is transmitted through the body member;
    a second source of light energy configured to emit substantially infrared free light energy;
    a light emitter connected to said second source of light energy and configured to introduce the infrared free light energy into the surgical site; and
    a detector for detecting the infrared light energy emitted by the light guide from within the body member.

7. The apparatus according to claim 6 wherein at least one of said first and second sources of light energy is configured to emit light energy in a pulsed pattern.

8. The apparatus according to claim 7 wherein said first source of light energy includes a light emitter configured to receive signals from a pulse generator and to emit pulsed light in response to the received signals.

9. The apparatus according to claim 1 wherein said second source of light energy is a source of endoscopic light energy and said light emitter is an endoscope.

10. The apparatus according to claim 6 further including a video camera sensitive to both received infrared free light energy and infrared light energy that is configured to generate image-defining video signals based on the received infrared free light energy and the infrared light energy emitted through the body member; and
    a video monitor configured to receive the video signals and display an image defined by the video signals.

11. A method of identifying a body member during a procedure in the vicinity of the body member, comprising the steps of:
    providing an infrared light generator;
    placing said infrared light generator in contact with the body member to be identified;
    actuating said infrared light generator so that infrared light energy is transmitted by the body member;
    illuminating the site of the procedure with light energy that is free of infrared light energy; and
    locating said body member by detecting said infrared light energy.

12. The method according to claim 11 further including the step of directing the infrared free light energy at the site of the procedure to a camera sensitive to both infrared and infrared free light energy.

13. The method according to claim 11 including the step of employing a camera for detecting the infrared light energy and further including the step of polarizing the light presented to the camera.

14. The method according to claim 11 wherein said infrared light generator is a light guide and the method includes the step of connecting said light guide to a source of infrared light energy;
    said step of placing said infrared light generator in contact with the body member includes a step of inserting said light guide into the body member; and
    said step of actuating said infrared light generator includes a step of activating said source of infrared light energy.

15. The method according to claim 11 including a step of actuating said infrared light generator to emit infrared light energy in a pulsed pattern.

16. The method according to claim 11 wherein said step of illuminating the site of the procedure with light energy that is free of infrared light energy includes the steps of:
    providing a light emitter connected to a source of light energy;
    actuating said source of light energy to direct light energy toward said light emitter;
    filtering an infrared light energy component from the light energy emitted by the source of light energy; and
    emitting substantially infrared free light energy from said light emitter toward the site of the procedure.

* * * * *

UNITED STATES PATENT AND TRADEMARK OFFICE
CERTIFICATE OF CORRECTION

PATENT NO. : 6,597,941 B2  Page 1 of 1
DATED : July 22, 2003
INVENTOR(S) : Mark G. Fontenot et al.

It is certified that error appears in the above-identified patent and that said Letters Patent is hereby corrected as shown below:

<u>Column 14,</u>
Line 10, change "Claim 1" to -- Claim 6 --

Signed and Sealed this

Seventeenth Day of February, 2004

JON W. DUDAS
*Acting Director of the United States Patent and Trademark Office*